United States Patent [19]

O'Dell

[11] Patent Number: 4,558,698

[45] Date of Patent: Dec. 17, 1985

[54] LASER CANALICULOSTOMY EYE-TREATMENT

[76] Inventor: Lawrence W. O'Dell, 34498 Deciwood Dr., Eugene, Oreg. 97401

[21] Appl. No.: 585,237

[22] Filed: Mar. 1, 1984

[51] Int. Cl.$^4$ .............................................. A61B 17/00
[52] U.S. Cl. ................................ 128/303.1; 128/395; 351/219
[58] Field of Search ........................ 604/115, 176, 136; 128/303.1, 395; 351/200, 219

[56] References Cited

U.S. PATENT DOCUMENTS 1,934,046  11/1933  Demarchi ........................... 604/115
3,548,830  12/1970  Goey et al. ......................... 604/176

Primary Examiner—Kyle L. Howell
Assistant Examiner—C. J. Graczyk
Attorney, Agent, or Firm—Kolisch, Hartwell & Dickinson

[57] ABSTRACT

A laser canaliculostomy eye-treatment method and device for promoting drainage of aqueous humor from the anterior chamber. According to one manner of practicing the invention, blood exiting the Canal of Schlemm is blocked by rim pressure applied externally to the eye to engorge the Canal with blood—thus to shift the Canal's apparent color toward that of blood. With engorgement established, a laser beam is directed in a pulse to create a fluid drainage passage connecting the anterior chamber and the Canal. According to another way of practicing the invention, the two steps just mentioned are preceded by preliminary use of a similar laser beam to create a small "passage-starting" crater in the trabecular meshwork adjacent the Canal at the location where the final passage is intended to lie. A device for facilitating blood engorgement of the Canal of Schlemm includes a Goldman lens receiving portion and a flange which produces pressure on the eye, restricting the flow of blood in the Canal. Means are provided for producing a partial vacuum between the Goldman lens and the eye.

6 Claims, 9 Drawing Figures

LASER CANALICULOSTOMY EYE-TREATMENT

BACKGROUND AND SUMMARY OF THE INVENTION

This invention pertains to a glaucoma treatment method, and more particularly to a method utilizing a laser to create a fluid drainage passage between the anterior chamber of an eye and the Canal of Schlemm and a device which assists a surgeon performing the treatment.

Glaucoma is a relatively common eye disease resulting from pressure build-up in the anterior chamber due to blocked or seriously impaired drainage of aqueous humor from this chamber.

Various techniques and medications which have been used in the past to alleviate symptoms of galucoma have proven often to be quite expensive and not entirely satisfactory, in that, among other things, recurrent treatment is necessary, and inconvenient.

A general object of the present invention is to provide a unique, relatively low-cost, effective method for treating a glaucoma condition.

More specifically, an object of the invention is to provide such a method which utilizes a pulse of light from a laser to create a fluid drainage passage (or more than one passage if need be) extending between the anterior chamber and the Canal of Schlemm, which passage effectively promotes the drainage of aqueous humor, and thus obviates damaging pressure build-up in the anterior chamber.

Another object of the invention is to provide a surgical device to assit a surgeon performing a treatment according to the invention.

Yet another object of the invention is to provide a method of the type generally mentioned which can be performed relatively simply on an outpatient basis, with long-term beneficial results.

According to one method of practicing the invention, blood normally draining from the Canal of Schlemm through the aqueous veins of Ascher is blocked by rim pressure applied externally to the periphery of the cornea—thus to engorge the Canal with blood. Such engorgement shifts the Canal's apparent color toward that of blood. With the Canal blood-engorged, and therefore readily recognizable, a laser beam pulse is directed, as through a conventional Goldman gonioscopic three-mirror lens, to create the desired drainage passage. One type of laser which has been found to be particularly effective is a laser utilizing a YAG (Yttrium-Aluminum-Garnet) crystal.

According to another method of practicing the invention, peferrably with blood engorgement of the Canal, a preliminary YAG laser beam pulse is directed toward the region where a final passage is desired, for the purpose of creating what is called herein a "passage-starting" crater in the trabecular meshwork which lies between the anterior chamber and the Canal of Schlemm. Thereafter, blood engorgement and laser impingement, as described according to the first method, are performed to complete the treatment procedure.

A vacuum-forming device, which receives a Goldman lens, may be used to facilitate blood engorgement.

As will be appreciated from the description which follows, treatment according to the method of the invention is accomplished cheaply, swiftly, and effectively.

Various other objects and advantages which are attained by the invention, will become more fully apparent as the description which now follows is read in conjunction with the accompanying drawings.

DETAILED DESCRIPTION OF THE INVENTION

Figure 1:
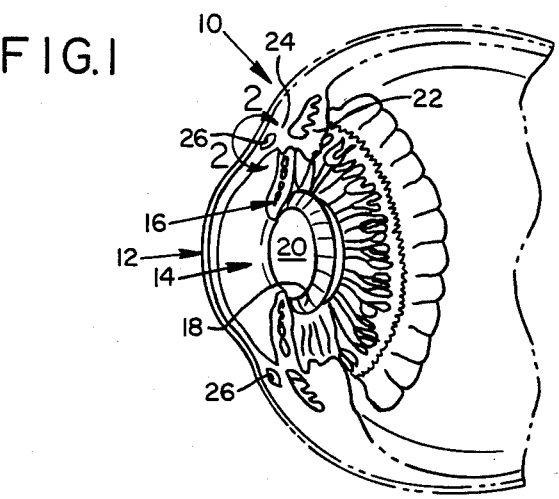
FIG. 1 is a simplified, fragmentary side cross section of the human eye.
Figure 2:
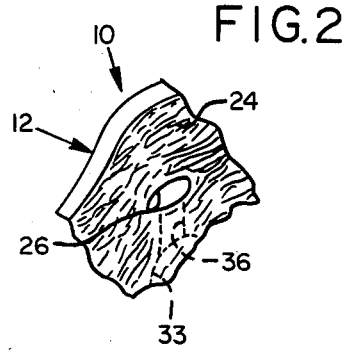
FIG. 2 is an enlarged fragmentary detail of the area generally encompassed by the curved, double-ended arrow in FIG. 1.
Figure 3:
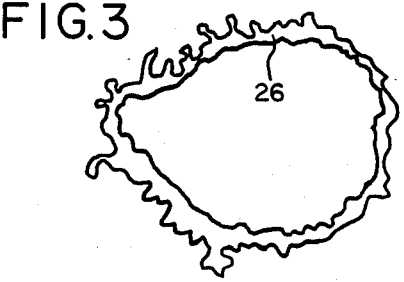
FIG. 3 is a front view of the Canal of Schlemm which extends generally circumferentially around the cornea in the eye—shown here removed from other structure in the eye.

Turning now to the drawings, and referring first to FIGS. 1 and 2, indicated generally at 10 is a human eye. At 12 in the eye is a cornea which defines the front side of an anterior chamber 14, the back side of which, generally speaking, is defined by an iris 16, a pupil 18 and a lens 20. Extending around both the lens and iris is the ciliary body 22. Distributed around the cornea, in the region where the cornea and iris meet, is a trabecular meshwork 24. Disposed within the trabecular meshwork, near the angle where the cornea and iris join (such angle sometimes being called the Corneo-scleral, or schleral, angle), is the Canal of Schlemm 26 which, generally speaking, circumferentially bounds the cornea. FIG. 3 shows the loop-like nature of the Canal as viewed from the front of eye 10, with the Canal removed from other structure in the eye.

In a normally healthy eye, there is, in the region of the scleral angle, a fluid communication "path" between the anterior chamber and Canal 26. This connection promotes regular drainage of excess aqueous humor in the anterior chamber through the trabecular meshwork and thence into the Canal of Schlemm. Canal 26 is also associated with the transport of venous blood in the eye.

In a glaucoma condition, drainage from the anterior chamber to the Canal of Schlemm through the trabecular meshwork is substantially impeded in the region of the scleral angle, and it is with respect to this condition that the method and device of the present invention are directed.

The main thrust of the invention is to promote non-surgically-invasive reestablishment of free drainage, in a glaucoma situation, between the anterior chamber and the Canal of Schlemm.

Figure 5:
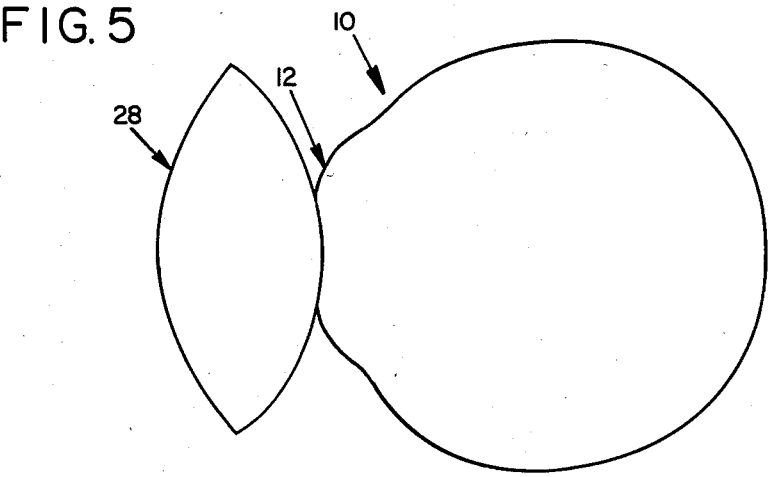
FIGS. 5-8, inclusive, illustrate, in simplified schematic form, successive stages in the treatment of the eye according to the method of the present invention.

Turning attention now to FIGS. 5-8, inclusive, a procedure preliminary to performing treatment according to the invention involves applying moderate pressure to the front of the eyeball, in a conventional manner, to soften the same, and to reduce some of the initial fluid pressure inside the anterior chamber. This procedure is illustrated in FIG. 5 where there is shown at 28 the inflated bladder of a conventional Honan instrument in contact with and pressing against cornea 12. Experience has shown that an appropriate way of using this procedure is to apply such an instrument with the same indicating a pressure of about 25-mm. Hg. for about one hour.

Figure 6:
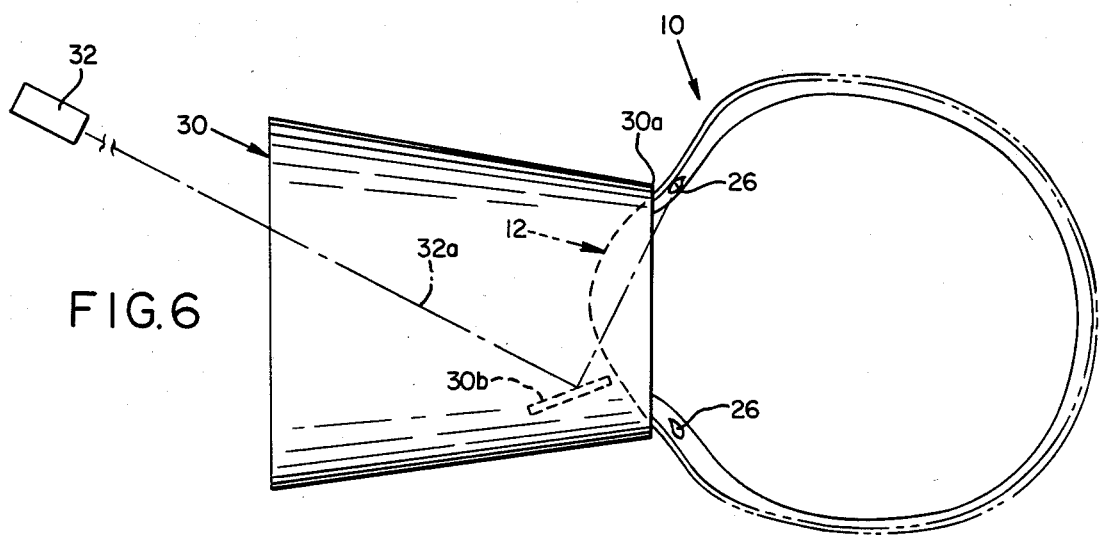

FIG. 6 in the drawings illustrates a preliminary method step which is employed according to one manner of practicing the invention. This step is useful in many applications, but is not required in all. According to this step, the narrow end 30a of a conventional, truncated-conical, Goldman, three-mirror, gonioscopic lens 30 is placed against the outside of the cornea as shown. End 30a is concave and substantially conformal to cornea 12. Then, employing one of the three mirrors inside lens 30, such being shown at 30b, a beam of light 32a from a yttriumm-aluminum-garnet (YAG) laser 32 is directed as a pulse through lens 30 and into the eye to create a laser beam-tissue impingement with the surface of the trabecular meshwork immediately adjacent the Canal of Schlemm at a location where it is desired to create, ultimately, a drainage passage. Laser 32 herein operates with a spot size of about 5.0-microns. This preliminary use of laser 32 creates what is referred to herein as a passage-starting crater 33 (seen in dashed outline in FIG. 2) in the trabecular meshwork.

A YAG laser is particularly effective for this procedure because it produces a highly focused concentration of laser energy in a small spot. This concentration of energy is sufficient to cause vaporization of tissue at the point where the laser beam impinges tissue in the travecular network. Although the temperature of the tissue at vaporization is approximately 2200° C., the point of impingement is so small that this extreme temperature is not readily transmitted to surrounding tissue. Additionally, as the impinged tissue vaporizes, there is a minute explosive effect which further helps to open the passage.

Figure 4:
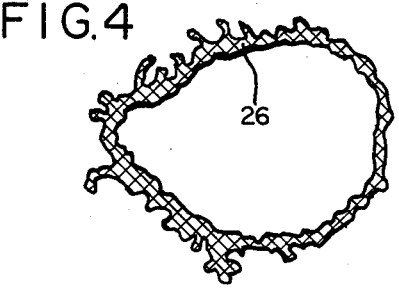
FIG. 4 is like FIG. 3, with the exception that it shows the Canal engorged with blood (illustrated by cross hatching) as a result of an important step performed in accordance with the invention.
Figure 7:
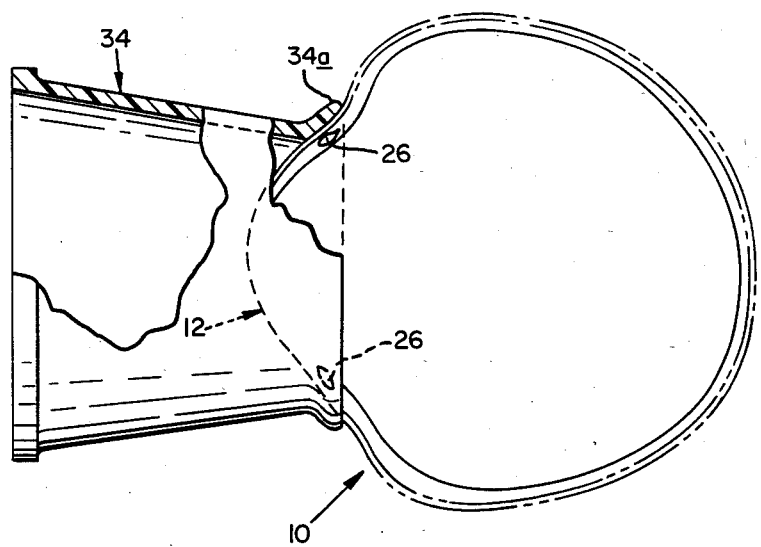

FIG. 7 illustrates an important method step which is common to all ways of practicing the present invention. Here, any suitable lens-receiving device, such as the hollow, truncated, conical device shown at 34, having a flared, beadlike, narrow end 34a is pressed firmly against the eye in a ring-like region surrounding the Canal of Schlemm. This action causes a build-up or engorgement of blood in the Canal of Schlemm so as to cause the Canal to take on the darkened red apparent color of blood. FIG. 4 illustrates this condition. The significance of this step is that it gives the Canal a color which is highly visible. This, in turn, enables the laser operator to see where to form a passage into the Canal of Schlemm with a YAG laser.

Figure 8:
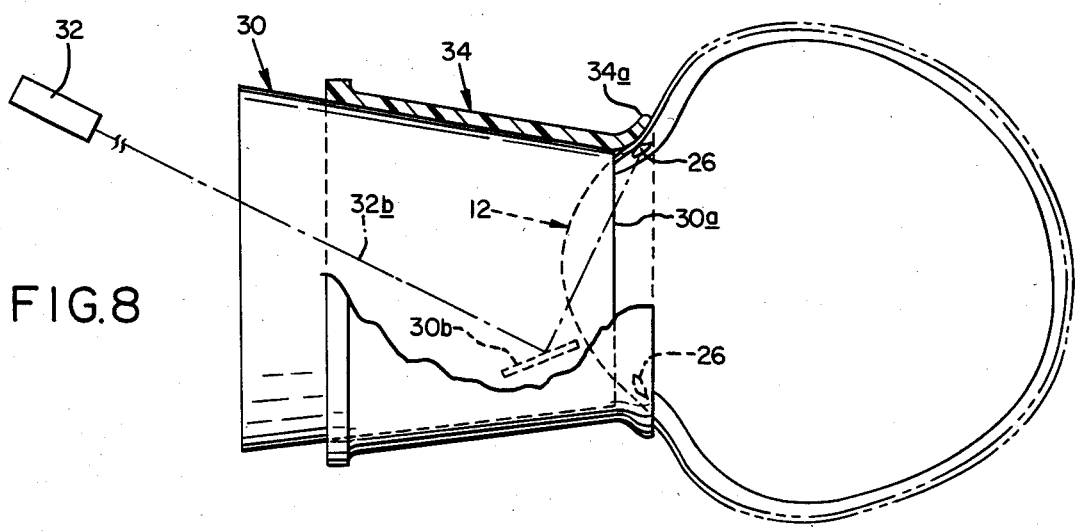

FIG. 8 illustrates a final step employed in all manners of practicing the invention. Here, with device 34 still held in place, the same lens 30 described above is nested in device 34, with its narrow end seated against the cornea. Lens 30 is again adjusted in such a manner that mirror 30b will deflect a beam from laser 32 toward the same spot impinged as described with reference to FIGS. 2 and 6. Laser 32 is then pulsed for a period of about 50n-seconds, and with a beam having the same spot size as described above. This beam, shown at 32b in FIG. 8, burns a passage 36 (shown in dash-dot outline in FIG. 2) which extends from the base of crater 33 into Canal 26.

In many instances, the creation of a single passage, like passage 36, is suitable to reestablish proper drainage from the anterior chamber to the Canal of Schlemm. In other instances, it may be necessary to re-employ treatment according to the invention to establish more than a single passage. After an initial passage is created, pressure in the anterior chamber of the eye is determined. If pressure in the anterior chamber is still unacceptably high, additional passages may be formed. If additional passages are formed, they should be in a quadrant opposed to or adjacent the one in which the first passage is located.

Figure 9:
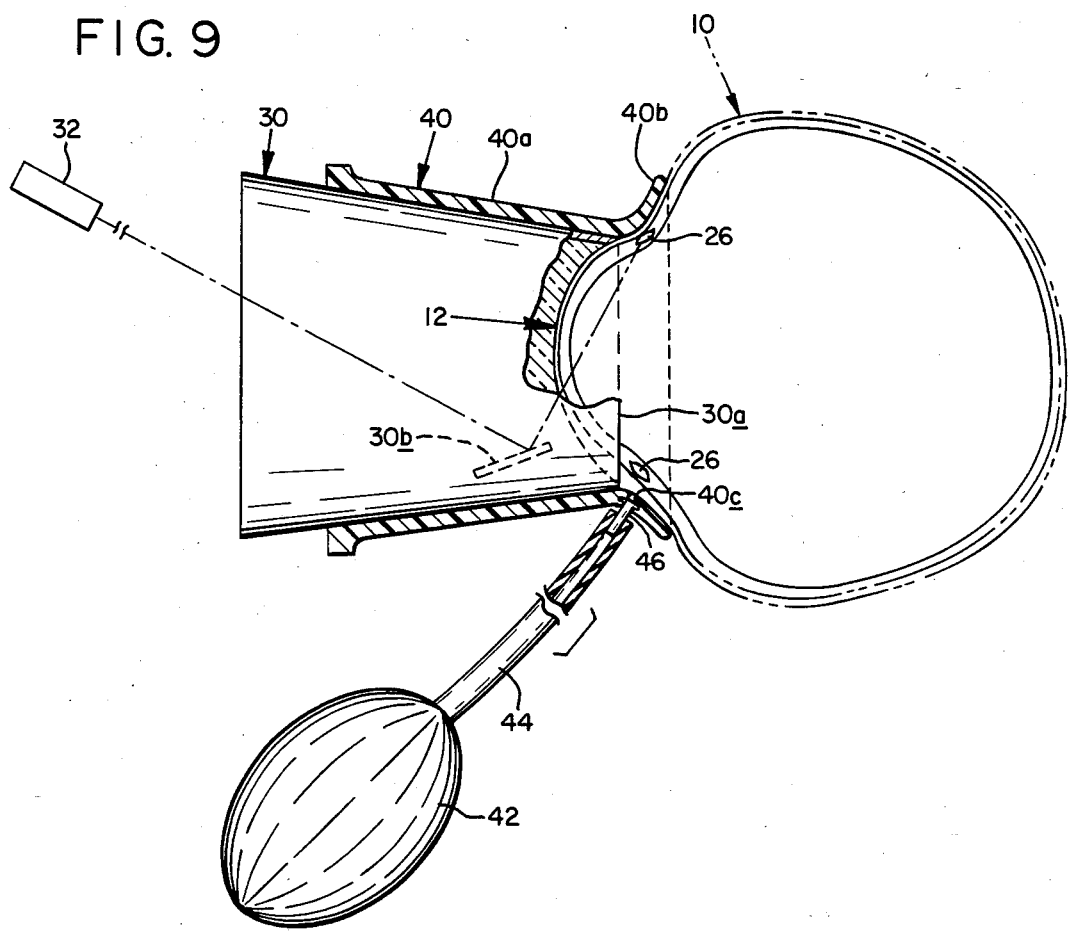
FIG. 9, shows a modified manner of practicing the invention, and a unique device therefor, involving the application of a partial vacuum in a space between the cornea and a conventional Goldman lens.

Turning now to FIG. 9, a modification of a lens-receiving device, which forms a partial vacuum, is shown (in cross section) generally at 40. Device 40 includes a hollow, truncated, conical portion 40a and a ring-like, elastomeric flange 40b, which may be placed in contact with the eye. Device 40 is sized such that lens 30 (shown partially broken away) may be received within conical portion 40a with its narrow end 30a held at a slight distance from the exterior or cornea 12.

A partial vacuum is formed within the device by vacuum producing means, which included a flexible suction bulb 42 which attached to device 40 by means of a flexible tube 44 and a tube-receiving fitting 46. Fitting 46 is suitably joined to portion 40a adjacent flange 40b, and communicates with the interior of the device via passage 40c.

Considering now a procedure employing the device shown in FIG. 9, initially, bulb 42 is filled with suitable gonioscopic solution, such as Gonioscopic Prism Solution manufactured by Alcon or, with a conventional saline solution. The Goldman lens is placed snugly in device 40 (as shown) prior to device 40 being pressed against the eye. With the assembly of lens in device 40 disposed upright, with their narrow ends facing upwardly, a small quantity of solution is pumped from bulb 42 and allowed to pool in the concave front portion of the lens, substantially up to the rim of flange 40b. This assemblage is then placed in intimate contact against the eye in such a manner that fluid in the pool just described bleeds from the flange region of device 40b to assure that no air bubbles exist in the ensuing space between the assemblage and the cornea. All of this is done with bulb 42 held somewhat compressed.

The assemblage of the lens and device 40 is now pressed, in the manner generally described earlier, against the eye to cause blood engorgement in the Canal of Schlemm. Substantially simultaneously, pressure on bulb 42 is released, causing the same to tend to draw fluid from the space between the assemblage and the cornea, thereby enhancing the vacuum effects of the assemblage against the eye.

With blood engorgement accomplished satisfactorily, laser 32 is employed in either one of the manners previously described, to complete the canaliculostomy treatment. The presence of a partial vacuum between the Goldman lens and the cornea will allow a stream of visible blood to enter the aqueous humor of the anterior chamber once a passage is completely formed into the Canal of Schlemm. Additionally, aqueous humor will be able to enter the canal which will cause a centripetal pulse in the Canal of Schlemm. The occurrence of blood flowing into the aqueous humor and flow of aqueous humor into the canal demonstrate a successively completed canaliculostomy.

Those skilled in the art will recognize that a number of modifications can be made in the treatment proposed by the present invention, where desired, to accomplish certain specific purposes.

One modification which might be desired in certain instances involves the diametral concentration of a laser beam employing a conventional plus-button on the larger or planer surface of lens 30. For example, such a button is capable of concentrating the original beam from a laser to approximately ½ of its nominal diameter. Such concentration, of course, has the effect of increasing power density in the incident laser beam.

Considering another modification, blood engorgement in the Canal may be enhanced by having a patient hold his or her breath with simultaneous diaphragm contraction immediately prior to energizing the laser during treatment. Alternatively, a patient may be fitted with an expandible mid-section cuff in order to increase overall venous blood pressure in the upper body.

The procedure may also be accomplished with the patient in a supine position. Although most lasers suitable for this procedure require the patient to be upright, a Q-switched YAG laser which operates with the patient lying down is available from American Medical Optics.

The procedure may also be accomplished utilizing a laser with an Alexandrite crystal. This laser produces a beam of light with a wavelength shorter than a YAG laser. The shorter wavelength light beam is operable with less power than a YAG laser and is also a more effective cutting tool.

While certain ways of practicing the invention have been described herein, those skilled in the art will appreciate that other variations and modifications are possible and may be employed without departing from the spirit of the invention.

It is claimed and desired to secure as Letters Patent:

1. A method employing a laser for effecting the drainage of aqueous humor from the anterior chamber of an eye to the Canal of Schlemm, said method comprising
   restricting the exit flow of blood from such Canal to cause the back-up collection therein of such blood, thus to shift the apparent color of the Canal toward the apparent color of such blood, and
   following said restricting, directing a beam from such a laser to create thereby a connective fluid passage extending generally between and communicating with an anterior chamber and the Canal.

2. The method of claim 1, wherein the flow of blood is restricted by applying a device to the eye and producing a partial vacuum between the device and the eye.

3. A method employing a laser for effecting the drainage of aqueous humor from the anterior chamber of an eye to the Canal of Schlemm, said method comprising
   directing a preliminary beam from such a laser to produce a crater in the trabecular meshwork, with such crater having a base adjacent, but short of, such Canal,
   restricting the exit flow of blood from such Canal to cause the back-up collection therein of such blood, thus to shift the apparent color of the Canal toward the apparent color of such blood, and
   following said restricting, directing a secondary beam from such a laser to create thereby a connective fluid passage extending between the base of such crater and the Canal.

4. The method of claim 2, wherein the flow of blood is restricted by applying a device to the eye and producing a partial vacuum between the device and the eye.

5. In combination with a Goldman Gonioscopic Lens, a device for facilitating blood engorgement in the Canal of Schlemm and receiving the Goldman lens therein during a canaliculostomy procedure comprising
   a Goldman lens receiving portion, formed as a hollowtruncated conical well, constructed and arranged to retain the lens a selected distance from a cornea,
   a resilient ring-like flange joined to said receiving portion at its narrow end, suitable for placement in contact with a cornea, sized to restrict blood flow out of the Canal of Schlemm, and
   suction producing means operably attached to said receiving portion adjacent said flange.

6. The device of claim 5, wherein said suction producing means includes a suction bulb.

* * * * *